United States Patent [19]

Zolla-Pazner et al.

[11] Patent Number: 5,731,189

[45] Date of Patent: Mar. 24, 1998

[54] HUMAN MONOCLONAL ANTIBODIES TO HUMAN IMMUNODEFICIENCY VIRUS

[75] Inventors: Susan Zolla-Pazner, New York; Miroslaw K. Gorny, Forest Hills, both of N.Y.

[73] Assignee: New York University, New York, N.Y.

[21] Appl. No.: 364,007

[22] Filed: Dec. 27, 1994

Related U.S. Application Data

[63] Continuation of Ser. No. 921,970, Aug. 4, 1992, abandoned, which is a continuation of Ser. No. 532,135, May 31, 1990, abandoned, which is a continuation-in-part of Ser. No. 409,986, Sep. 19, 1989, abandoned, which is a continuation-in-part of Ser. No. 316,744, Feb. 28, 1989, abandoned.

[51] Int. Cl.$^6$ .............................. C12N 5/10; C12N 5/08; C07K 16/10
[52] U.S. Cl. .......................... 435/240.2; 435/240.27; 530/387.9; 530/388.15; 530/388.35
[58] Field of Search ..................... 435/247.2, 240.2, 435/240.27, 172.2; 530/388.15, 388.35, 391.7, 387.9; 424/85.6, 85.8

[56] References Cited

FOREIGN PATENT DOCUMENTS

| 0251612 | 1/1988 | European Pat. Off. |
| 0 251 612 | 7/1988 | European Pat. Off. ......... C12P 21/00 |
| 0 279 688 | 8/1988 | European Pat. Off. ......... A61K 37/02 |
| 8602383 | 4/1986 | WIPO |

OTHER PUBLICATIONS

Modrow et al., Computer-Assisted Analysis of Envelope Protein Sequences of Seven Human Immunodeficiency Virus Isolates: Prediction of Antigenic Epitopes of Conserved and Variable Regions, *J. Virol.* 61:570–578, 1987.
Banapour et al., Characterization and Epitope Mapping of a Human Monoclonal Antibody Reactive with the Envelope Blycoprotein of Human Immunodeficiency Virus, *J. Immunol*, 139:4027–4033, 1987.
Grunow et al., The High Efficiency, Human B Cell Immortalizing Heteromyeloma CB–F7 (Production of Human Monoclonal Antibodies to Human Immunodeficiency Virus); *J. Immunol. Methods*, 106:257–265, 1988.
Evans et al., Human Monoclonal Antibody Directed Against gag Gene Products of the Human Immunodeficiency Virus, *J. Immunol*, 140:141–143, 1988.
Zolla–Pazner et al., Potential Use of Serotherapy in the Prevention and Treatment of Infection with the Human Immunodeficency Virus, *J. Virol. Methods*, 17:45–53, 1987.
Desgranges et al., Monoclonal Antibodies to HIV in a Non–Infected, Immunised Voluntee; *The Lancet*, pp. 935–936, Apr. 23, 1988.

Zolla–Pazner et al., Long–Term Antibody–Producing Cells from the Blood of Seropositive Subjects, Fourth International Conference on AIDS, 1988, Abstract No. 2515.
Zolla–Pazner et al., Production of Antibody by Circulating B Cells of HIV–Seropositive Subjects, Third International Conference on AIDS, 1987, Abstract No. TP. 110.
Fahey et al. Clin. exp. Immunol. 88: 1–5, 1992.
Koup et al. J. Virology 63(2): 584–590 13 Jan. 1989.
Casali et al. Science 234: 476–479, 1986..
Teeuwsen et al. J. Cellular Biochem Suppl. 12B: 44, 1988.
Sugano et al. BBRC ISS: 1105, Sep. 1988.
Davis et al. The lancet, Apr. 23, 1988, 935.
Steinitz et al. Nature 269: 420, 1977.
Ho, J. Virology 61: 2024, 1987.
Matthews et al., PNAS 83: 9709, 1986.
Blumberg et al. J Infectious Diseases 156: 878, 1987.
Mitsuya, Science (Oct. 1984) 226: 172–174.
Norman, Science (Dec. 1985) 230: 1355–1358.
Ho, J. Virology (Jun. 1987) 61(6): 2024–2028.
Modrow, J. Virol (Feb. 1987) 61(2) 570–578.
Sandstrom, Drugs (Sep. 1987) 34: 372–390.
Roland Grunow et al. "The high efficiency, human B cell immortalizing heteromyeloma CB–F7. Production of human monoclonal anitbodies to human immunodeficiency virus, Journal of Immunological Methods", vol. 106 (1988) pp. 257–265.
L Madisen et al. "Expression of the Human Immunodeficiency Virus gag Gene in Insert Cells", Journal of Virology, vol. 158 pp. 248–250, (1987).
Rook et al., Sera from HTLV–III/LAV Antibody–Positive Individuals Mediate Antibody–Dependent Cellular Cytotoxicity Against HTLV–III/LAV–Infected T Cells, The Journal of Immunology, vol. 138, 1064–1067, Feb. 15, 1987.
Tyler et al., Identification of sites Within gp41 that Serve as Targets for Antibody–Dependent Cellular Cytotoxicity by Using Human Monoclonal Antibodies, The Journal of Immunology, vol. 145, 3276–3282, Nov. 15, 1990.
Teeuwsen et al., Production and Characterization of Human Monoclonal Antibody, Reactive with a Conserved Epitope on gp41 of Human Immunodeficiency Virus Type I, AIDS Research and Human Retroviruses, vol. 6, No. 3, 1990.

*Primary Examiner*—Lila Feisee
*Assistant Examiner*—Nancy A. Johnson
*Attorney, Agent, or Firm*—Browdy and Neimark

[57] ABSTRACT

Disclosed herein are eleven human lymphoblastoid cell lines producing monoclonal antibodies directed against human immunodeficiency virus (HIV) proteins gp41 and p24. Also disclosed are methods for treating HIV-infected individuals using the human monoclonal antibodies and pharmaceutical formulations comprising effective amounts of the human monoclonal antibodies.

21 Claims, 10 Drawing Sheets

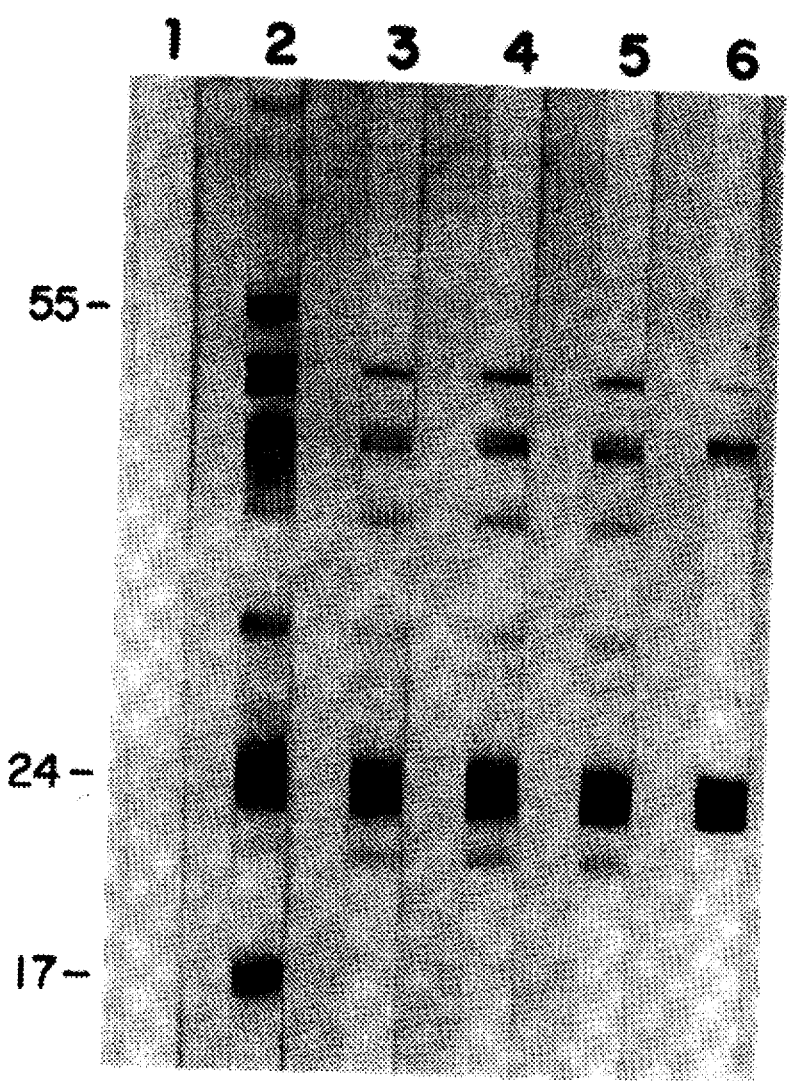

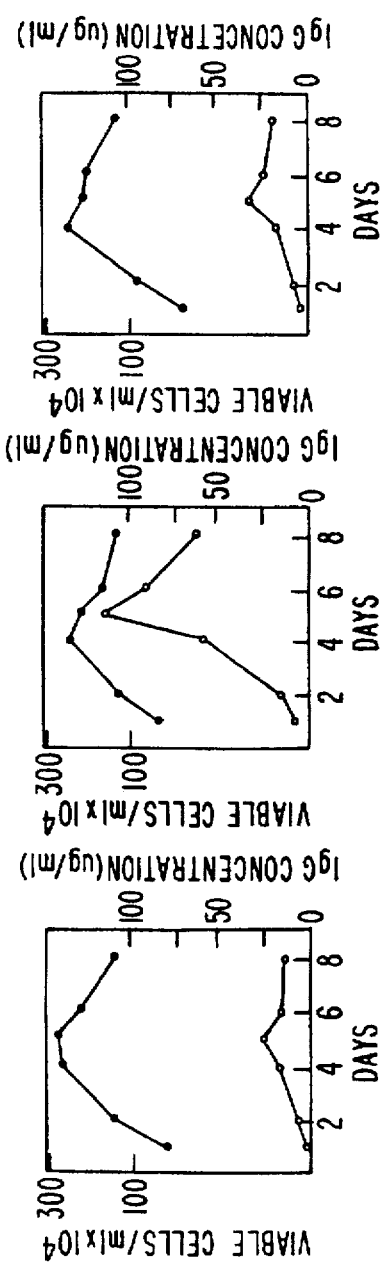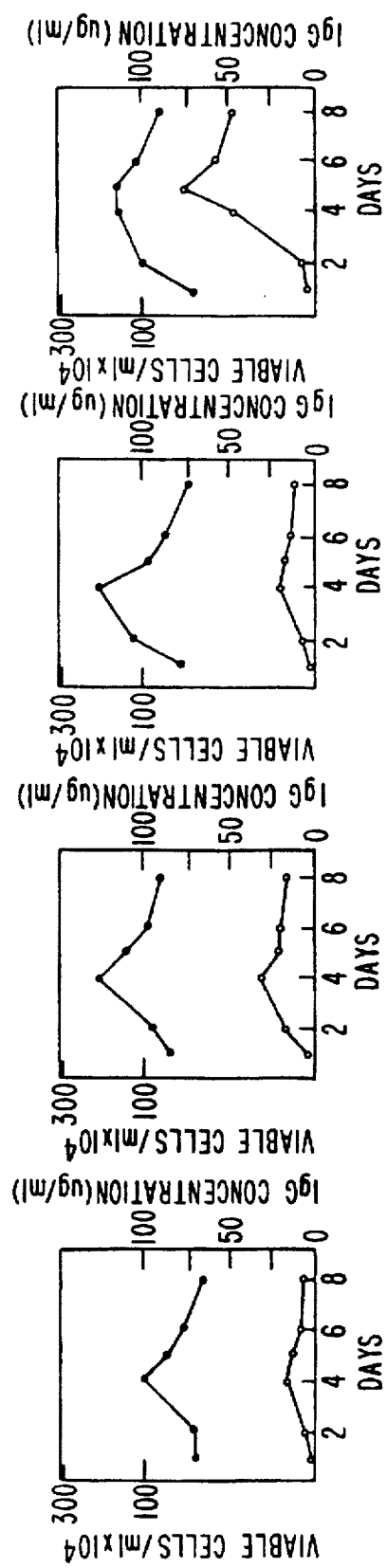
FIG. 3a FIG. 3b FIG. 3c FIG. 3d FIG. 3e FIG. 3f FIG. 3g

FIG. 5

```
ATGAAACACCTGTGGTTCTTCCTCCTGCTGGTGGCAGCTCCCAGATGGGTCCTGTCCCTC
----.----+----.----+----.----+----.----+----.----+----.----+   60
TACTTTGTGGACACCAAGAAGGAGGACGACCACCGTCGAGGGTCTACCCAGGACAGGGAG m   k   h   l   w   f   f   l   l   l   v   a   a   p   r   w   v   l   s   l

CTGCAACTACAGGAGTCCGGCTCAGGACTGGTGAAGCCTTCACAGACCCTGTCCCTCACC
----.----+----.----+----.----+----.----+----.----+----.----+   120
GACGTTGATGTCCTCAGGCCGAGTCCTGACCACTTCGGAAGTGTCTGGGACAGGGAGTGG l   q   l   q   s   s   g   s   g   l   v   k   p   s   q   t   l   s   l   t

TGCACTGTCTCTGGTGGCTCCATCAGCAGTGGTGGGTATGCCTGGACCTGGATCCGGCAG
----.----+----.----+----.----+----.----+----.----+----.----+   180
ACGTGACAGAGACCACCGAGGTAGTCGTCACCACCCATACGGACCTGGACCTAGGCCGTC c   t   v   s   g   g   s   i   s   s   g   g   y   a   w   t   w   i   r   q

CCCGCCGGGAAGGGACTGGAGTGGATTGGCCGTATCTATTCTACTGGGACCACCGCCTTC
----.----+----.----+----.----+----.----+----.----+----.----+   240
GGGCGGCCCTTCCCTGACCTCACCTAACCGGCATAGATAAGATGACCCTGGTGGCGGAAG p   a   g   k   g   l   e   w   i   g   r   i   y   s   t   g   t   t   a   f

AACCCCGCCCTCAAGGGTCGATCCACCATTTCAGTAGACACGTCCAAGACCAAGTTCTTC
----.----+----.----+----.----+----.----+----.----+----.----+   300
TTGGGGCGGGAGTTCCCAGCTAGGTGGTAAAGTCATCTGTGCAGGTTCTGGTTCAAGAAG n   p   a   l   k   g   r   s   t   i   s   v   d   t   s   k   t   k   f   f

CTGAGACTGACGTCTGTGACCCGCGCAGACACGGCCACTTATTTCTGTGCCAGAGTCACG
----.----+----.----+----.----+----.----+----.----+----.----+   360
GACTCTGACTGCAGACACTGGGCGCGTCTGTGCCGGTGAATAAAGACACGGTCTCAGTGC l   r   l   t   s   v   t   r   a   d   t   a   t   y   f   c   a   r   v   t

TTGACAAGTCGAGTTGTAGGTCGTTACTTTGACTCATGGGGCCAGGGACTCCTGGTCACC
----.----+----.----+----.----+----.----+----.----+----.----+   420
AACTGTTCAGCTCAACATCCAGCAATGAAACTGAGTACCCCGGTCCCTGAGGACCAGTGG l   t   s   r   v   v   g   r   y   f   d   s   w   g   q   g   l   l   v   t

GTCTCCTCA
----.----+  429
CAGAGGAGT v   s   s
```

FIG. 6

```
ATGAAACACCTGTGGTTCTTCCTCCTGCTGGTGGCAGCTCCCAGATGGGTCCTGTCCCTC
----.----+----.----+----.----+----.----+----.----+----.----+   60
TACTTTGTGGACACCAAGAAGGAGGACGACCACCGTCGAGGGTCTACCCAGGACAGGGAG m   k   h   l   w   f   f   l   l   l   v   a   a   p   r   w   v   l   s   l

CTGCAACTACAGGAGTCCGGCTCAGGACTGGTGAAGCCTTCACAGACCCTGTCCCTCACC
----.----+----.----+----.----+----.----+----.----+----.----+  120
GACGTTGATGTCCTCAGGCCGAGTCCTGACCACTTCGGAAGTGTCTGGGACAGGGAGTGG l   q   l   q   e   s   g   s   g   l   v   k   p   s   q   t   l   s   l   t

TGCACTGTCTCTGGTGGCTCCATCAGCAGTGGTGGGTATGCCTGGACCTGGATCCGGCAG
----.----+----.----+----.----+----.----+----.----+----.----+  180
ACGTGACAGAGACCACCGAGGTAGTCGTCACCACCCATACGGACCTGGACCTAGGCCGTC c   t   v   s   g   g   s   i   s   s   g   g   y   a   w   t   w   i   r   q

CCACCAGGGAAGGGCCTGGAGTGGATTGGATTCATCTATTATTATGGAGGCGCCTCTTAC
----.----+----.----+----.----+----.----+----.----+----.----+  240
GGTGGTCCCTTCCCGGACCTCACCTAACCTAAGTAGATAATAATACCTCCGCGGAGAATG p   p   g   k   g   l   e   w   i   g   f   i   y   y   y   g   g   a   s   y

AACCCGTCCCTCGAGAGTCGAGTCACCTTGTCAGCAGACACTTCCAAGAACCAAATCTCC
----.----+----.----+----.----+----.----+----.----+----.----+  300
TTGGGCAGGGAGCTCTCAGCTCAGTGGAACAGTCGTCTGTGAAGGTTCTTGGTTTAGAGG n   p   s   l   e   s   r   v   t   l   s   a   d   t   s   k   n   q   i   s

CTTCAGCTGACCTCTGCGACCGCCGCGGACACGGCCGTATATTATTGTGCCAGATCCTTT
----.----+----.----+----.----+----.----+----.----+----.----+  360
GAAGTCGACTGGAGACGCTGGCGGCGCCTGTGCCGGCATATAATAACACGGTCTAGGAAA l   q   l   t   s   a   t   a   a   d   t   a   v   y   y   c   a   r   s   f

GGCGTCTATTTCTACCTCGATCTCTGGGGCCGTAGCACCCTGGTCTCTGTCTCCTCA
----.----+----.----+----.----+----.----+----.----+----.--     417
CCGCAGATAAAGATGGAGCTAGAGACCCCGGCATCGTGGGACCAGAGACAGAGGAGT g   v   y   f   y   l   d   l   w   g   r   s   t   l   v   s   v   s   s
```

HUMAN MONOCLONAL ANTIBODIES TO HUMAN IMMUNODEFICIENCY VIRUS

This application is a continuation of application Ser. No. 07/921,970, filed Aug. 4, 1992, now abandoned, which was a continuation of application Ser. No. 07/532,135, filed May 31, 1990, now abandoned, which was a continuation-in-part of application Ser. No. 07/409,986, filed Sep. 19, 1989, now abandoned, which in turn was a continuation-in-part of application Ser. No. 07/316,744, filed Feb. 28, 1989, now abandoned.

The government has rights to this invention by virtue of funding from grant AI-72658 from the National Institutes of Health.

BACKGROUND OF THE INVENTION

The human immunodeficiency virus (HIV) has been implicated as the causative agent of acquired immune deficiency syndrome (AIDS). Two different serotypes of the virus have been identified to date: HIV-1 and HIV-2. It is currently believed that the majority of individuals that become infected with HIV eventually will develop AIDS and are likely to succumb to fatal infections and/or malignancies. At this time it is estimated that approximately 1.5 million individuals have been infected by HIV in the United States alone.

Several avenues have been explored to treat individuals afflicted with AIDS or HIV infections. The antiviral drug azidothymidine (AZT) has been found to produce both clinical and immunological improvements upon short term administration to patients afflicted with AIDS and ARC (AIDS Related Complex—a prodrome of the disease) and to decrease the mortality rate and frequency of opportunistic infections. Although clinical benefits are achieved with AZT, it is costly. A further drawback is that significant drug toxicity often accompanies administration of AZT. This may necessitate blood transfusions and/or reduction of the AZT dosage, or in some instances, discontinuance of AZT therapy altogether. Nonetheless, AZT is the only drug currently authorized for the treatment of AIDS.

An alternative treatment that is currently under evaluation involves administration of one or more lymphokines. Interferon (particularly gamma-interferon) and interleukin-2 are currently being studied for possible use in the treatment of HIV infections. However, the preliminary results of early clinical trials are not promising. Patients receiving lymphokine therapy often suffer serious side effects including low blood pressure, nausea and diarrhea.

It has been proposed to use monoclonal antibodies of defined specificities directed against HIV proteins expressed in infected individuals as therapeutic agents. These proteins are part of the virus particles and are expressed by HIV infected cells and are designated inter alia as p24 and gp41. The identification and isolation of gp41 is described in U.S. Pat. No. 4,725,669 of M. Essex, issued Feb. 16, 1988 as is its use in the treatment and diagnosis of AIDS. The identification of p24 has been described in Allan, J. S. et al., *Science* 228: 1091, 1985. However, the use of monoclonal antibodies for the treatment of HIV infections has been hampered because only a limited number of murine and rat monoclonal antibodies to HIV proteins are available. In addition, none of the currently available monoclonal antibodies directed against HIV proteins are of human origin. Administration of murine antibodies to humans can cause dangerous life threatening immunologic reactions, and such antibodies may not be effective in binding to the target HIV proteins in humans.

Stable human cell lines which produce monoclonal antibodies directed against HIV would be useful for treating and/or diagnosing individuals infected with the virus. However, human monoclonal antibodies and particularly those directed against HIV have proven to be far more difficult to produce than those of either rat or mouse origin. Amongst the explanations for this problem are: (a) the most available source of lymphocytes from humans, the peripheral blood, normally contains few antibody producing cells and in some instances, none at all; (b) transformation of antibody producing cells can be achieved using Epstein-Barr virus (EBV), but the level of antibody production by these transformed cells is often low and unstable; (c) stability of antibody production can be enhanced, as can levels of antibody production, by fusion of EBV-transformed lines to mouse myeloma cells but, these 'heterohybridomas' readily delete human chromosomes and immunoglobulin production is often lost; and (d) fusion of normal or transformed B cells to human lymphoblastoid lines or to heteromyelomas stabilizes antibody production but, until recently, few satisfactory parent lines of this cell type have been available.

OBJECTS OF THE INVENTION

It is an object of the present invention to provide human lymphoblastoid cell lines producing monoclonal antibodies directed against protein components of HIV.

Another object of the present invention is to provide diagnostic and therapeutic agents comprising human monoclonal antibodies directed against HIV proteins which have a low non-specific toxicity for use in the diagnosis and treatment of individuals infected with HIV.

A further object of the present invention is to provide a method for treating individuals suffering from HIV infections by administering human monoclonal antibodies directed against protein components of HIV to said individual.

A still further object of the present invention is to provide pharmaceutical formulations for treating individuals suffering from HIV infections.

These and other objects of the present invention will be apparent to those of ordinary skill in the art in light of the following specification.

SUMMARY OF THE INVENTION

The present inventors have discovered new monoclonal antibodies for the treatment, prophylaxis and diagnosis of human immunodeficiency virus (HIV) infections. These are human monoclonal antibodies directed against HIV proteins gp41 and p24 which are expressed by infected cells. The human monoclonal antibodies of the present invention may be used as diagnostic agents, directly as therapeutic agents, as the basis for vaccines or to form conjugates by covalent coupling with cytotoxic agents, specific anti-HIV drugs or radionuclides (the antibody/toxin conjugates are alternatively referred to herein as immunotoxins) for use in the diagnosis and treatment of individuals that have been exposed to or infected with HIV. The present invention provides stable human lymphoblastoid cell lines which secrete human monoclonal antibodies directed against HIV proteins gp41 and p24. The invention also provides human monoclonal antibodies directed against HIV proteins p24 and gp41.

Another aspect of the present invention comprises a method for treating a mammal infected with HIV comprising administering to a mammal in need of such treatment an effective amount of a human monoclonal antibody directed against HIV.

In a further aspect, the present invention comprises pharmaceutical formulations comprising an effective amount of a human monoclonal antibody to HIV proteins.

BRIEF DESCRIPTION OF THE DRAWINGS

FIG. 2 is a Western blot analysis of human sera and a subset of the monoclonal antibodies of the present invention.

FIGS. 3a, 3b, 3c, 3d, 3e, 3f and 3g are graphs of the growth kinetics and immunoglobulin production of a subset of the human lymphoblastoid cell lines of the present invention which produce monoclonal antibodies directed against HIV.

FIG. 5 is a chart depicting the cDNA sequence of the mRNA encoding the heavy chain of human monoclonal antibody 120-16 and the deduced amino acid sequence of the heavy chain.

FIG. 6 is a chart depicting the cDNA sequence of the mRNA encoding the heavy chain of human monoclonal antibody 98-6 and the deduced amino acid sequence of the heavy chain.

DETAILED DESCRIPTION OF THE INVENTION

Figure 1:
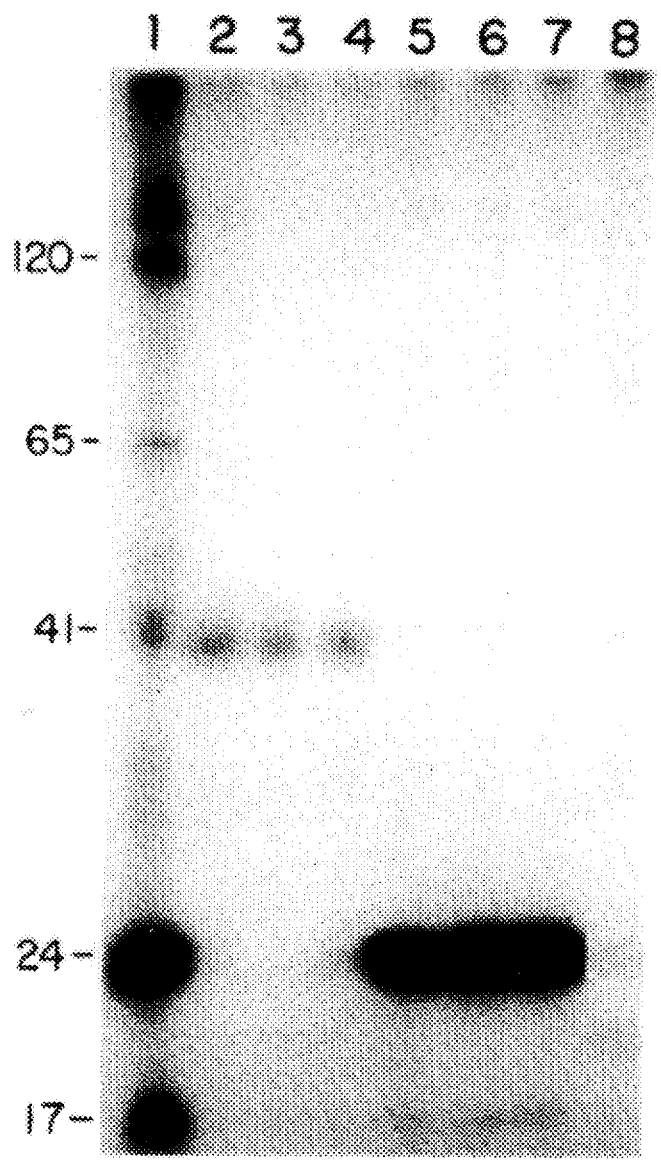
FIG. 1 is a radio-immunoprecipitation assay of $^{125}$[I]-labelled HIV lysate with serum from an HIV-infected subject or with antibodies from a subset of the human monoclonal antibody producing cell lines of the present invention.

All literature references and patents cited in this specification are hereby incorporated by reference in their entirety.

The present inventors have isolated fourteen novel stable human lymphoblastoid cell lines producing monoclonal antibodies directed against HIV encoded proteins. The antibodies of the invention are useful in the prophylaxis of HIV and in the diagnosis, and treatment of humans suffering from HIV infections. These human monoclonal antibodies are directed against HIV protein gp41 and protein p24 (and the precursors and decomposition products of such proteins).

gp41 is a viral membrane glycoprotein expressed on the surface of infected cells and is a product of the env gene of HIV (as described in Essex, M., U.S. Pat. No. 4,725,669 issued Feb. 16, 1988). p24 is a viral core protein and is a product of the HIV gag gene (as described in Allan, J. S. et al., supra).

The human monoclonal antibodies of the present invention may be employed as the antibody component in the conventional diagnostic assays of the type used to determine if a patient has been exposed to, or infected with, HIV. Example 6 below illustrates the use of the antibodies of the invention in a diagnostic assay. Administered to humans, the antibodies can provide passive immunization of HIV-infected individuals. In addition, the antibodies of the invention can serve prophylactically for administration to non-infected, high-risk individuals (such as health care workers who have been exposed via a needle stick to HIV). The antibodies of the invention also can serve as research tools for epitope mapping of HIV proteins gp41 and p24.

A particularly important use of the human monoclonal antibodies of the present invention is for administration to HIV infected expectant mothers. All of the antibodies of the present invention are of the IgG isotype (see below). Since IgG's can pass through the placenta and reach the fetus in utero, passive administration of the antibodies of the present invention to HIV-infected pregnant women would provide effective therapy for the fetus.

The human monoclonal antibodies may be conjugated to cytotoxic agents and used as immunotoxins (as described in Vitetta, E. S. et al., Science 238: 1098–1104, 1987) or incorporated onto the surface of liposomes containing anti-HIV drugs or toxins to specifically target such drugs or toxins to infected cells. As employed herein the term "immunotoxin" refers to a conjugate of an antibody with one or more toxins, drugs, radionuclides or cytotoxic agents. Among the cytotoxic agents that may be conjugated to the antibodies of the present invention are ricin, diphtheria toxin and radionuclides. Ricin is an extremely potent toxin produced by the beans of the plant Ricinus communis. In a typical treatment employing the human monoclonal antibodies of the present invention as immunotoxins, the antibody (which binds to a protein that is expressed by HIV-infected cells) is conjugated to a toxin (e.g. ricin) that is toxic to the HIV-infected cell (and to non-infected cells as well). By coupling the cytotoxic agent to the antibody, a high level of toxic efficacy can be achieved against the target cell with a markedly lower level of non-specific toxicity. The use of the toxic agent is possible because the human monoclonal antibodies to which the agent is coupled will carry the agent directly to the target (in this case, HIV-infected cells), thereby sparing non-infected cells from the toxin. Techniques that may be employed to conjugate human monoclonal antibodies, including those of the present invention, to cytotoxic agents are described in detail in Vitetta et al., supra and in European Patent Application Ser. No. 279,668, published Aug. 24, 1988 of Genentech, Inc. At page 9, lines 35–36, the latter publication states:

In a further embodiment toxin-conjugates are made with Fab or (F(Ab')$_2$ fragments. Because of their relatively small size these fragments can better penetrate tissue to reach infected cells.

The human lymphoblastoid cell lines (which produce the monoclonal antibodies of the present invention) were formed by immortalizing lymphocytes obtained from HIV-seropositive patients by infecting such lymphocytes with Epstein Barr Virus (EBV) in vitro. Initially, blood was obtained from 58 HIV-seropositive individuals, peripheral blood mononuclear cells were obtained and incubated overnight with EBV. The EBV infected cells were cultured at 80,000 cells per well in microtiter wells for 3–4 weeks and assayed for anti-HIV antibody production using a non-commercial ELISA (see below) and a commercial ELISA employing HIV-coated beads. The specificity of each positive reaction obtained by the ELISA was confirmed by testing for their non-reactivity on identical beads coated with bovine serum albumin (BSA).

Approximately 9% of the lymphoblastoid cell cultures tested positively in the non-commercial ELISA. After expansion the positive wells were cultured for two more weeks. It was found that 2.4% tested positively for HIV proteins by ELISA and 0.67% proved to be specific for HIV by virtue of their non-reactivity on the BSA beads. The anti-HIV antibodies produced were found to be directed against gp41 or p24 and had sufficient avidity to show reactivity by ELISA, Western blot, radio-immunoprecipitation and/or immunofluorescence.

Therefore, all of these monoclonal antibodies would be useful in diagnostic assays for HIV. The stable clones were then subcultured 2 to 3 times at 10 or 100 cells per well with irradiated human lymphoblastoid feeder cells and expanded into tissue culture flasks.

In a second round of immortalization/selection, peripheral blood mononuclear cells from another 36 HIV-seropositive individuals were obtained, immortalized by EBV infection and assayed for anti-HIV production as above. Four stable lymphoblastoid cell lines were obtained producing monoclonal antibodies: 120-16, 126-6, 126-50, 167-7 and 191-3 against gp41, and 134-F6 against p24.

In addition, one cell line, 98-4.3, producing monoclonal antibodies against p24, was obtained from positive cultures derived from the first group of 58 patients described above. The culture was subcultured twice after several unsuccessful trials and is presently stable in culture.

The characteristics of the human monoclonal antibodies produced by the lymphoblastoid cell lines of the present invention are described in Table III of Example 5 below.

The present inventors have performed some epitope mapping of the human monoclonal antibodies of the present invention. For example, it can be seen from the data presented in Example 5, Table III below that monoclonal antibodies 50-69 and 98-43 bind to the same epitope cluster (i.e. amino acids falling between residues 579 and 613) whereas 98-6 binds to a different region (amino acids falling between residues 642 and 692). However, monoclonal antibodies 50-69 and 98-43 differ in their epitope specificity as demonstrated by the fact that 50-69 binds to peptide 599–613 whereas 98-43 binds to peptides 579–604. Three of the anti-p24 antibodies have been tested (i.e. 71-31, 91-5 and 91-6). All bind to the same region of p24 (131–198).

All of the human monoclonal antibodies of the present invention directed against gp41 (i.e. 50-69, 98-6, 98-43, 120-16, 126-6, 126-50, 167-7 and 191-3) mediated antibody dependent cellular cytotoxicity (ADCC) as shown in Table III below. This is a most important finding in that serotherapy (e.g. passive immunization) and seroprophylaxis in animal retroviral models have been shown to be mediated by ADCC (Plata, F. et al., Cell 48: 231, 1987; Weinhold, K. J. et al, J. Natl. Cancer Inst. 75: 717, 1985). The ADCC immune response is directed by specific antibodies and involves mobilization of effector cells e.g. cytotoxic T-cells, monocytes, and killer cells, against specific targets. It is believed that the ability to mount an ADCC response will be important for serotherapy and seroprophylaxis in HIV infections also.

The fourteen lymphoblastoid cell lines thus obtained are stable in culture and produce human monoclonal antibodies directed against targets on HIV which are produced in vivo in infected patients.

The human monoclonal antibodies of the present invention are all of the IgG isotype and may be recovered from the supernatants of monoclonal antibody producing lymphoblastoid cell cultures and purified by conventional methods known in the art for the purification of IgG. Such methods include Protein-A Sepharose chromatography, a combination of Affigel Blue (Bio-Rad, Richmond, Calif.) and Protein-A Sepharose chromatography, or High Performance Liquid Chromatography (HPLC).

The eleven stable lymphoblastoid cell lines described in Examples 1–6 below produce human monoclonal antibodies which are directed against unique epitopes which are expressed in HIV-infected patients. Although some epitope mapping has been performed (see Table III in Example 5 below), further epitope mapping will determine the exact specificity of each of the monoclonal antibodies and may reveal targets on the HIV gp41 and p24 protein molecules which can be candidates for vaccine production.

The human monoclonal antibodies of the present invention are directed against either immunodominant (common) or non-dominant epitopes of the gp41 and p24 viral proteins. As employed in this specification, the term "immunodominant" refers to an antigenic determinant that most patients respond to the production of antibodies. Antibodies 50-69 and 120-16, directed against gp41, are to immunodominant epitopes. These two antibodies may be employed for passive immunizations and/or diagnostic reagents. Antibodies 71-31 and 91-5, directed against p24, are to non-dominant epitopes.

Lymphoblastoid cell lines 91-5 and 126-6 (producing human monoclonal antibodies directed against p24 and gp41, respectively) have been deposited on Feb. 24, 1989, prior to the filing date of the parent application, U.S. Ser. No. 07/316,744, from which the present application claims priority with the American Type Culture (ATCC 12301 Parklawn Drive, Rockville, Md. 20852) and have received Accession numbers CRL 10038 and CRL 10037, respectively.

The classification of the antibodies of the invention into an immunodominant or non-dominant grouping was accomplished by inhibition testing as described in Example 6 below. In this assay, sera collected from HIV seropositive individuals were used to inhibit the binding of biotinylated monoclonal antibodies directed against HIV proteins to their respective antigens. Presented below in Example 7 and in FIGS. 5 and 6 are the cDNA sequences encoding the mRNA for the heavy chains of human monoclonal antibodies 120-16 and 98-6, respectively. An alternative embodiment of the present invention encompasses these nucleic acid sequences, polypeptides encoded by these sequences and nucleic acid sequences which hybridize with these sequences under stringent hybridization conditions (as disclosed in Sambrook, J. et al., Molecular Cloning: A Laboratory Manual, 2nd edition, pp 9.50–9.51 and 11.45–11.55, Cold Spring Harbor Laboratory Press, Cold Spring Harbor, N.Y., 1989).

Of the monoclonal antibodies to p24 and gp41, only those to gp41 mediated antibody-dependent cellular cytotoxicity (ADCC). In vitro cytotoxicity studies revealed that the most active induced significant levels of killing was at minimum concentrations of 15–250 ng Ab/ml. ADCC was assayed using peripheral blood mononuclear cells (MNC) as effectors and the CEM.NKR cell line, infected with HTLV-IIIB, MN and RF (viral strains), as targets.

Two monoclonal antibodies to gp41 and one monoclonal antibody to p24 were purified and coupled to the deglycosylated A chain of ricin. The anti-p24 immunotoxin (IT) did not kill infected or uninfected H9 or U937 cells at concentrations up to 20 ug Ab/ml. IT made with monoclonal antibody to gp41, however, reduced protein synthesis in infected H9 cells by 50% (IC50) at concentrations of 500 ng/ml. The IC50 of anti-gp41 IT for infected U937 cells was 1000 ng/ml. In the presence of chloroquine, the IC50 of these immunotoxins (ITs) was 5–10 ng/ml.

When employed to treat individuals infected by HIV or suffering from AIDS, the human monoclonal antibodies of the present invention (having a specificity and a binding affinity for HIV proteins p24 and gp41) may be administered as passive immunization agents in effective amounts broadly ranging between about 200 mg and about 15 grams and preferably between 50 mg and 1 gram. The antibodies of the invention are administered parenterally, and preferably via the intravenous or intramuscular route. A typical treatment regimen would comprise administration of an effective amount of antibody administered over between about one week and about 6 months. The number of treatments required to control a patient's disease will vary from individual to individual, depending upon the severity and stage of the illness and the individual characteristics of each patient being treated. The total dose required for each treatment may be administered by multiple doses or in a single dose. The human monoclonal antibodies may be administered alone or in conjunction with other HIV treatments, such as AZT, in order to control a patient's disease. The anti-HIV treatment may be administered one or two times a week or more as determined by the patient's condition and the stage of the patient's disease.

The human monoclonal antibodies of the present invention can be incorporated into conventional pharmaceutical formulations for use in treating individuals that are afflicted with HIV or for prophylaxis in individuals at risk for such infections. The pharmaceutical formulations of the invention comprising an anti-HIV effective amount, range between about 200 mg and about 15 grams, of the human monoclonal antibodies of the present invention identified in Examples 1–6 below. The quantity of effective dose applied by each injection is relatively unimportant since the total dosage can be reached by administration of one or a plurality of injections. In addition, such formulations may comprise pharmaceutically-acceptable carriers, diluents, salts and other materials well-known in the art. Isotonic saline, sterile water, 10% maltose, human serum albumin, glycine or other pharmaceutically-acceptable materials may be used as diluents, carriers or solvents in preparing the pharmaceutical formulations comprising the human monoclonal antibodies of the present invention.

The present invention is described below in specific working examples which are intended to illustrate the invention without limiting its scope.

EXAMPLE 1

Immortalization of Human B-cells

Blood was obtained from 58 HIV-seropositive individuals who were intravenous drug users or homosexuals. The presence of antibody to HIV in the blood was determined using a commercial enzyme-linked immunosorbent assay (ELISA) (Organon-Teknika Bio-Enzabead HTLV-III ELISA, Durham, N.C.) and confirmed by Western blot (Novapath Immunoblot Assay, Bio-Rad, Hercules, Calif. and Biotech/DuPont, DuPont, Wilmington, Del.). The disease status of patients was established on the basis of an immunologic staging system as described by Zolla-Pazner et al. (*Proc. Nat. Acad. Sci. USA* 84: 5404, 1987):

| Scale Score | T4/T8 ratio | #T4/mm | #lymphocytes/mm |
|---|---|---|---|
| 0 | >1.0 | >500 | >1500 |
| 1 | <1.0 | >500 | >1500 |
| 2 | <1.0 | <500 | >1500 |
| 3 | <1.0 | <500 | <1500 |

Peripheral blood mononuclear cells collected from the 58 patients were obtained by centrifugation of heparinized blood, diluted 1:1 with RPMI-1640 and centrifuged on Histopaque (Sigma, St. Louis, Mo.) at 300×g for 30 minutes. Cells at the medium/Histopaque interface were recovered, washed three times and incubated overnight at a density of $2 \times 10^6$ cells/ml with the filtered supernatant from the EBV-transformed marmoset cell line B95-8 (*Proc. Nat. Acad. Sci. USA* 70: 190, 1973, available under Accession Number CRL 1612 from the American Type Culture Collection, ATCC, Rockville, Md.). Lymphocytes were then washed once and cultured in RPMI-1640 medium (M.A. Bioproducts, Walkersville, Md.) supplemented with 10% fetal calf serum (Hyclone Labs, Logan, Utah) 2 mM L-glutamine, 100 U/ml penicillin, and 100 micrograms/ml streptomycin (complete medium) for four weeks in 96-well plates (Costar, Cambridge, Mass.) at 80,000 cells per well.

EXAMPLE 2

Isolation and Screening of Lymphoblastoid Cell Lines for Anti-HIV Antibody Production After screening for anti-HIV antibody production by a non-commercial ELISA (see below), positive cultures were expanded into wells of 24-well tissue culture plates (Costar) and cultured for two more weeks. All initial and expanded cultures were fed at weekly intervals with complete medium. Cultures with supernatants showing specific reactivity to HIV were then subcultured one to two times at doubling dilution on feeder layers of irradiated GK-5 human lymphoblastoid cells (derived from a variant of GM1500; Satoh, J. et al., *N. Engl. J. Med.* 309: 217, 1983) which had been exposed to 3000 Rads of gamma-radiation. Stable clones were then subcultured one to three times at 10 to 100 cells per well on feeder cells and then expanded into flasks.

Thus, initial cultures of immortalized B-cells (hereinafter referred to as lymphoblastoid cell lines) were established and further characterized as described below.

The screening of the initial cultures in 96-well plates was performed using a non-commercial ELISA. Immulon 2 plates (Dynatech, Chantilly, Va.) were coated overnight at 4° C. with 4 micrograms/ml of HTLV-III$_B$ lysate (purchased from Electro-Nucleonics, Inc., Silver Spring, Md.) diluted in carbonate buffer, pH 9.8. Plates were washed three times with phosphate buffered saline, pH 7.2, containing 0.05% Tween 20 (PBS-Tween). The culture supernatants to be assayed (0.1 ml per well) were then added and incubated for 90 or 120 minutes at 37° C. Subsequently, plates were washed with PBS-Tween and incubated with goat anti-human immunoglobulin conjugated to alkaline phosphatase (Organon Teknika-Cappel, Malvern, Pa.) for another 90 minutes at 37° C. The plates were washed again with PBS-Tween and the substrate, p-nitrophenyl phosphate in 10% diethanolamine, was added for 30 minutes. The reaction was terminated with 25 microliters of 1N NaOH and the absorbance was read at 405 nm in an automated ELISA reader (MR 600 Microplate Reader, Dynatech).

The specificity of the antibody binding was assessed by testing the supernatants for reactivity against HIV-coated beads (Bio-EnzaBead) and against uncoated beads (obtained from Organon Teknika Cappel) which were then coated with bovine serum albumin (BSA, Sigma Chemical Co.) by incubating the beads in 1.25% BSA diluted in PBS for 1 hour at room temperature. Reactivity with HIV-coated beads, but not with BSA-coated beads, was used as a criterion for specificity. Further analysis of the specificity of the monoclonal antibodies was then carried out by Western blot using a commercially-available kit (Bio-Rad, Richmond, Calif.) and by radioimmunoprecipitation (RIP). RIP assays were carried out using the method of Pinter and Honnen (*J. Immunol. Methods*, 112: 235–241, 1988). Briefly, 30 micrograms of HTLV-III$_B$ lysate (purchased from Organon-Teknika), was labeled with $^{125}$[I] using the Bolton-Hunter reagent (New England Nuclear, Boston, Mass.). Bound label was separated from free label on a Bio-Gel P-4 column (Bio-Rad). Fifty microliters of culture supernatant were incubated with $5\times10^6$ cpm of the labeled lysate for 1 hour at 37° C., then 50 microliters of 10% fixed *Staphylococcus aureus* (Pansorbin, Calbiochem, La Jolla, Calif.) was added. The immunoprecipitate was washed three times by centrifugation and the air-dried pellet was resuspended in buffer, boiled for 3 minutes and electrophoresed on a 10% SDS polyacrylamide gel. The gels were dried and exposed for one to three days to X-Omat S film (Kodak, Rochester, N.Y.).

The class and light chain type of anti-HIV antibody was determined by ELISA. For these assays, microtiter plates (Immulon 2) were coated with 4 micrograms/ml of HIV lysate (Electro-Nucleonics) and then incubated with culture supernatants. The type of antibody binding to HIV was determined using the following alkaline phosphatase-coupled antibodies: goat anti-human IgG (gamma specific), goat anti-human kappa chain and goat anti-human lambda chain (Organon Teknika-Cappel, Malvern, Pa.). The subtype of the monoclonal antibody was also analyzed by ELISA using alkaline phosphatase-labeled mouse monoclonal antibodies against the four subclasses of human IgG (Zymed, San Francisco, Calif.).

Immunoglobulin quantitation was also performed by ELISA. Immulon 2 plates were coated with goat anti-human IgG (gamma specific) and incubated with culture supernatants. Bound IgG was detected with alkaline phosphatase-labeled goat anti-human IgG (gamma specific). Affinity-purified human IgG (Cappel) was used to produce standard curves.

A total of 14,329 cultures in microtitre wells were established using cells derived from the 58 subjects. Approximately half of these cultures were derived from three serial bleeds from a single subject (with a scale score of 1) over a period of three months. The remaining wells were established using cells derived from 57 subjects whose scale scores ranged from 0 to 3. The results of this procedure are shown in Table I below.

TABLE I

QUANTITATIVE RESULTS OF THE PROCEDURE USED TO PRODUCE HUMAN MONOCLONAL ANTIBODIES TO HIV

|  | No. of wells | % positive wells |
|---|---|---|
| 1. Infection of PBMC with EBV | 14,329 | (100) |
| ↓ 4 weeks |  |  |
| Screen for anti-HIV by Non-commercial ELISA | 1,290 | 9.0 |
| 2. Expand positive wells |  |  |
| ↓ 2 weeks |  |  |
| Screen for anti-HIV by: |  |  |
| Non-commercial ELISA | 573 | 4.0 |
| Commercial ELISA | 340 | 2.4 |
| Screen for specificity (reactive HIV, unreactive with BSA) | 97 | 0.67 |
| Screen for reactivity by RIP | 57 | 0.40 |
| 3. Subculture positive wells by doubling dilution (10,000–10 cells/well) |  |  |

TABLE I-continued

QUANTITATIVE RESULTS OF THE PROCEDURE USED TO PRODUCE HUMAN MONOCLONAL ANTIBODIES TO HIV

|  | No. of wells | % positive wells |
|---|---|---|
| ↓ 4–6 weeks |  |  |
| Screen by commercial ELISA | 16* | 0.11* |
| 4. Subculture positive wells at (100 and 10 cells/well) |  |  |
| ↓ 4–6 weeks |  |  |
| Screen by commercial ELISA | 7* | 0.05* |

*No. and % of positive plates from subcultures of individual wells which contain at least one antibody positive well.

After four weeks, 9% of the wells displayed antibody production as revealed by the non-commercial ELISA (Table I). After expansion, only 2.4% of the original cultures continued to produce antibody reactive with a commercial ELISA kit and only one-quarter of these (0.67% of the original 14,329 cultures) were producing antibodies which reacted specifically with HIV.

To determine whether the severity of disease in the cell donor affected the number of cultures able to produce antibodies and the specificity of antibody produced, the seropositive cell donors were categorized with respect to disease status using the immunologic staging system of Zolla-Pazner et al. (supra) and the results are shown in Table II below.

TABLE II

CHARACTERISTICS OF CELL CULTURES DERIVED FROM PATIENTS AT DIFFERENT STAGES OF HIV INFECTION

| Scale Score | No. of patients | No. of wells | No. of positive wells (Includes HIV-specific & non-specific reactivity) | No. of wells with HIV-specific antibody | No. of clumps per well+ |
|---|---|---|---|---|---|
| HIV-seronegative patients: |  |  |  |  |  |
| 3 | 637 | 0 | 0 | 7.3 |  |
| HIV-seropositive patients: |  |  |  |  |  |
| 0 | 4 | 725 | 18 (2.4%) | 6 (0.8%) | 0.92 |
| 1 | 13 | 8,789 | 180 (2%) | 66 (0.7%) | 0.88 |
| 2 | 20 | 2,792 | 54 (1.9%) | 16 (0.5%) | 0.65 |
| 3 | 21 | 2,023 | 88 (4.3%) | 9 (0.4%) | 0.22 |
|  | 58 | 14,329 | 340 2.4% | 97 0.67% | 0.66 |

*Specificity of anti-HIV antibodies were assessed by commercial ELISA using HIV-coated and BSA-coated beads.
+B cells transformed by EBV stick together and create characteristic clumps of cells which were quantitated microscopically.

The results, shown in Table II, revealed that cultures obtained from patients with a scale score of 3 (severe immunodeficiency) gave a higher percentage of antibody producing wells than patients with lesser scale scores. However, only 10% (9/88) of reactive wells from the cells of stage 3 patients were specifically reactive with HIV whereas 30–37% of wells from cells of patients with scale scores of 0–2 were specifically reactive with HIV. Thus, after six weeks of culture, cells from patients with lower scale scores produced a higher percentage of wells containing HIV-specific antibody.

Analysis of antibodies from ELISA-positive expanded cultures was carried out by RIP. Only 59% of supernatants from these cultures were also positive on RIP analysis. RIP analysis demonstrated that, out of 57 supernatants, 44 showed reactivity to env-encoded proteins, 11 to gag proteins and 2 to reverse transcriptase.

Therefore, specific lymphoblastoid cell lines were isolated and further cloned as described below.

EXAMPLE 3

Specificity and Reactivity of the Human Monoclonal Antibodies of a Subset of the Present Invention The 57 cell lines mentioned above were then cloned by doubling dilution from 10,000 to 10 cells per well. Wells with the lowest cell concentration which were producing antibodies were then picked and cloned at 100 or 10 cells per well. Using this procedure, seven cell lines, 3 producing anti-gp41 antibodies and 4 producing anti-p24 antibodies were established which have been cloned from one to three times at 100 or 10 cells per well. The reactivities of the antibodies from these lines are shown in FIGS. 1 and 2.

All seven of the cell lines of this Example produced antibodies of the IgG subtype as shown in FIG. 1 and Table III. As shown in FIG. 1 below, HIV-positive control serum and 6 out of 7 of the monoclonal antibodies tested reacted with [$^{125}$I]-labeled HIV lysate by radioimmunoprecipitation. In FIG. 1, the following results are shown: lane 1, reactivity with serum from an HIV-infected subject, lane 2, reactivity with antibody from cell line 50-69, lane 3, reactivity with antibody from cell line 98-6, lane 4, reactivity with antibody from cell line 98-43, lane 5, reactivity with antibody from cell line 71-31, lane 6, reactivity with antibody from cell line 91-5, lane 7, reactivity with antibody from cell line 91-6 and lane 8, reactivity with antibody from 98-4.9. The molecular weights of the major viral proteins are shown on the left in kilodaltons. Antibody from three of the cell lines bound to env-encoded protein gp41 (lines 50-69, 98-6 and 98-43, lanes 2-4 respectively). Antibodies from three of the cell lines bound to gag encoded protein p24 (lines 71-31, 91-5, 91-6, lanes 5-7 respectively). Antibodies from 98-4.9 (lane 8) were unreactive by RIP since IgG3, the subtype of this antibody, does not bind to Protein A and is therefore not precipitated. Antibody from all 4 of these anti-gag cell lines were also tested by Western blot (FIG. 2) and react with gag products.

In FIG. 2, Western Blot strips were used to show the reactivity of serum from a normal control (lane 1), an HIV-infected subject (lane 2), and of supernatant from cell lines 71-31 (lane 3), 91-51 (lane 4), 91-6 (lane 5), and 98-4.9 (lane 6). Western blot analysis showed that 3 monoclonal antibodies reacted with p24 and with known gag precursor p55 and intermediate p40. All four antibodies reacted with p24 and also reacted with a breakdown product of p24 which migrated with a mobility of approximately 22 kilodaltons (kd); three of the four anti-gag monoclonal antibodies also reacted with additional intermediate precursors which were noted with a mouse monoclonal antibody and which had mobility of approximately 37, 31 and 28 kd.

Studies of the growth characteristics and level of antibody production of each line were performed. Each cell line was initially cultured in replicate wells at $0.5 \times 10^6$ cells/ml for 1-8 days. The number of cells and the amount of immunoglobulin produced is shown in FIG. 3. In FIG. 3, at each time point, separate wells were used to test for viable cell number (closed circles) and for secreted human IgG (open circles). Cell lines studied were 50-69(a), 98.6(b), 98-43(c), 71-31 (d), 91-5(e), 91-6(f) and 98-4.9(g).

Peak cell density was noted at 4 days with maximum densities of 1.0 to $2.4 \times 10^6$ cells/ml. The doubling time of cells in log phase ranged from 40-61 hours. The concentration of immunoglobulin produced varied widely, generally peaking at day 5 of culture and ranging from 9-112 micrograms/ml.

It should be noted that cell line 98-4.9 has not been stabilized with respect to the production of human monoclonal antibodies.

EXAMPLE 4

Generation of Additional Lymphoblastoid Cell Lines Producing Human Monoclonal Antibodies to HIV Peripheral blood mononuclear cells were obtained from another 36 HIV-seropositive individuals, the cells immortalized by EBV infection, screened and selected as in Examples 1-3 above. Positive cultures were expanded, subcultured by doubling dilution and again subcultured one to three times at 10 to 100 cells per well. Four stable lymphoblastoid cell lines producing human monoclonal antibodies were obtained as follows: 120-16, 126-6 and 126-50 directed against gp41; and 134-F6 directed against p24.

Each of the monoclonal antibodies of this Example were tested for their specificities by means of commercial ELISA (the supernatants were reactive with HIV-coated beads and unreactive with BSA-coated beads), by radioimmunoprecipitation and by Western Blot as in Example 3 above. The characteristics of these human monoclonal antibodies are shown in Table III below.

EXAMPLE 5

Characterization of the Human Monoclonal Antibodies of the Present Invention

The specificity and biological activities of the human monoclonal antibodies of the present invention are summarized in Table III below.

TABLE III

Characteristics of human monoclonal antibodies against HIV

| Cell line | Isotype, Subclass and Light Chain Type | RIP | ELISA | | | Western Blot | | Function | | | Approx. Epitope Region |
|---|---|---|---|---|---|---|---|---|---|---|---|
| | | | ENV9 | PE3 | p121 | r-gp41 | r-p24 | Neutr. | Enhanc. | ADCC | |
| 50–69 | IgG$_2$k[1] | gp41 | + | – | + | + | – | – | – | + | 599–613[2], a |
| 98–6 | IgG$_2$k | gp41 | + | – | – | + | – | – | – | + | 642–692 |
| 98–43 | IgG$_2$k | gp41 | + | – | ± | + | – | – | – | + | 579–604[2] |
| 120–16 | IgG$_2$k | gp41 | + | – | – | NT[3] | – | – | + | + | 567–649 |
| 126–6 | IgG$_2$k | gp41 | + | – | + | NT | – | – | – | + | 567–649 |
| 126–50 | IgG$_2$k | gp41 | + | – | – | NT | – | – | – | + | NT |
| 191–36 | IgG$_1$l | gp41 | | | | | | | | | |
| 167–7 | IgG$_1$l | gp41 | | | | | | | | | 661–683 |
| 71–31 | IgG$_1$l[4] | p24 | – | – | – | NT | + | – | – | – | 131–198[5] |
| 91–5 | IgG$_1$l | p24 | – | – | – | NT | + | – | – | – | 131–198 |
| 91–6 | IgG$_1$l | p24 | – | – | – | NT | + | – | – | – | 131–198 |
| 98–4.9[6] | IgG$_3$l | p24 | – | – | – | NT | NT | – | – | – | NT |
| 98–4.3 | IgG$_1$l | p24 | NT | NT | NT | NT | NT | NT | NT | NT | NT |
| 134-F6 | IgG$_3$k | p24 | NT | NT | NT | NT | NT | NT | NT | NT | NT |

[1] k = Kappa
[2] The Modrow numbering system according to J. Virol. 61: 570, 1987.
a Tested for reactivity on LABSYSTEM Kit
[3] NT = Not tested
[4] l = Lambda
[5] The numbering system according to Wain-Hobson, it al., Cell 40: 9, 1985
[6] This lymphoblastoid cell line has not been stabilized with respect to the production of monoclonal antibodies In Table III, epitope mapping was performed using recombinant antigens using a Western Blot and ELISA formats. Viral Neutralization and enhancement assays were performed as in *J. Clin. Micro.* 26: 231, 1988. ADCC assays were performed according to Lyerly, H. K. et al. *AIDS and Human Retroviruses* 3: 409–422, 1987. Western Blot analysis was performed using recombinant p24 or gp41 (obtained from Organon-Teknica).

ELISA's were performed using cloned gp41 antigens. ENV9 is a cloned gp41 protein encompassing residues 461 to 761 (obtained from DuPont, Wilmington, Del.). PE3 is a 286 amino acid sequence from gp120 (obtained from DuPont, Wilmington, Del.), p121 contains residues 561–649 of gp41 (obtained from Centocor, Malvern, Pa.).

As can be seen in Table III above, all of the anti-gp41 human monoclonal antibodies of the present invention were of the IgG isotype and mediated antibody dependent cellular cytotoxicity (ADCC).

In addition, epitope mapping showed that five of the anti-gp41 antibodies bound to different epitopes on the viral protein. Monoclonal antibody 50-69 bound to residues 599–613 ; monoclonal antibody 98-6 was directed against a peptide encompassing residues 642–692; monoclonal antibody 98-43 bound to a peptide encompassing gp41 residues 579–604; monoclonal antibody 120-16 bound residues 644–663; and monoclonal antibody 167-7 bound to residues 661–683. The numbering system for the gp41 peptide is according to *J. Virol.* 61: 570, 1987.

All three of the anti-p24 monoclonal antibodies tested (71-31, 91-5 and 91-6) bound to a HIV p24 peptide encompassing residues (131–198 (the numbering system according to Wain-Hobson et al. *Cell* 40: 9, 1987) (Table III).

Finally, none of the monoclonal antibodies of the present invention were able to neutralize the infectivity of HIV and one (120-16) enhanced viral pathogenicity.

EXAMPLE 6

Inhibition Testing of the Monoclonal Antibodies of the Present Invention

Presented below is an example of the use of the monoclonal antibodies of the present invention in a diagnostic assay for HIV.

Immulon 2 plates (Dynatech) were coated with 0.5 micrograms/well of an HIV lysate diluted in 0.05M carbonate buffer, pH 9.6 for 2 hours at 37° C., and overnight at 4° C. After washing the plates with phosphate buffered saline, pH 7.4, containing 0.05% Tween (PBS-Tween), 100 microliter samples of human sera, obtained from HIV seropositive or seronegative individuals were added to each well after dilution to 1:10 to 1:1000. The plates were incubated at room temperature overnight and washed three times with PBS-Tween. A predetermined dilution of biotinylated monoclonal anti-HIV antibodies (see below) was then added in a volume of 100 microliters and the plates incubated for 2 hours at 37° C. The wells were washed three times with PBS-Tween and the reaction developed by adding an avidin-biotinylated-horseradish peroxidase complex (Vector Labs) and incubated for 30 minutes at 37° C. After washing 5 times with PBS-Tween, 2,2'-azino-di-[3-ethyl-benzthiazoline sulfonate] (ABTS) was added as substrate and incubated for 30 minutes at room temperature. The optical density of each well was read in an ELISA reader at 410 nm.

Biotinylation of the monoclonal antibodies to HIV was performed as follows. Each monoclonal antibody was partially purified by ammonium sulfate precipitation and/or chromatography on Protein A-Sepharose. After dialysis against 0.1M sodium bicarbonate, 75 microliters of N-hydroxyl-succinimidobiotin (5 mg in 1 ml of DMSO) was added to 1 ml of the antibody at a protein concentration of 5 mg/ml. The reaction was allowed to proceed at room temperature with shaking for 3 hours and then dialyzed against phosphate buffered saline, pH 7.4. The biotinylated monoclonal antibodies were stored at –25° C. in 50% glycerine before use.

Figure 4:
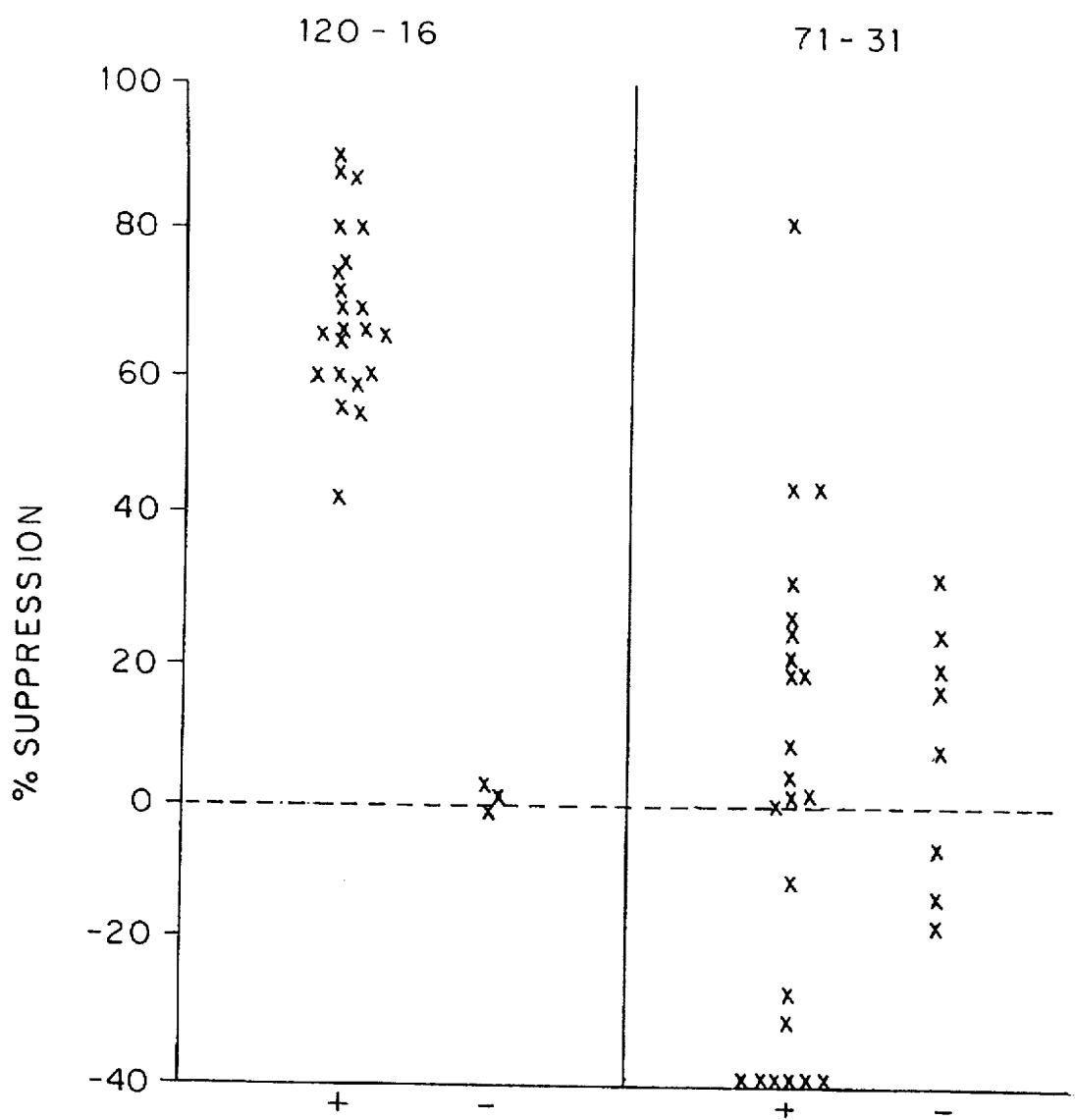
FIG. 4 is a graph showing the inhibition testing of monoclonal antibodies 120-16 and 71-31.

The results of the inhibition tests are shown in FIG. 4. In FIG. 4, the seronegative sera is designated (–) and the seropositive (+).

The data presented in FIG. 4 show that antibodies 120-16 and 71-31 are directed against immunodominant epitopes and non-dominant epitopes respectively. Thus, seropositive sera are able to compete for the binding of labeled antibody 120-16 to the HIV lysate defining the epitope of this monoclonal antibody as immunodominant. Non-dominance was established for the epitope with which 71-31 reacts as a result of the inability of most seropositive sera to compete with this antibody for binding to the HIV lysate.

EXAMPLE 7

Sequencing of the cDNA Encoding the mRNA for Monoclonal Antibodies 120-16 and 98-6

The sequence of the cDNA encoding the mRNA for the heavy chain of monoclonal antibodies 120-16, 126-6 and 98-6 was determined as set forth below.

Single Stranded-cDNA Synthesis

Total RNA was extracted from cells as described in Sans, I. et al. *J. Immunol.* 142:83, 1989. Single stranded c-DNA (ss-cDNA) was synthesized using AMV reverse transcriptase (Molecular Genetics Resources, Tampa, Fla.) as the enzyme and oligo-dT (Pharmacia LKB Biotechnology Inc., Piscataway, N.J.) as the primer. The quantity of the synthesized ss-cDNA was assessed by measuring the incorporation of $^{32}$P-dCTP.

Polymerase Chain Reaction

Polymerase chain reactions (Saiki, R. K. et al. *Science* 239: 487, 1988) were done using the method recommended by the manufacturer (Perkin Elmer Cetus, Norwalk, Conn.). The two primers used were as follows:

5' ATGAAA CAC CTG TGG TTC 3'     (1)

These sequences were from the $V_H$IV leader sequence as disclosed in Kabat, E. et al. (*Sequences of Proteins of Immunologic Interest*, Department of Health and Human Services, Washington, D.C., 1987).

5' CAG GGG GAA GAC GCA TGG 3'     (2)

These sequences were from the 3' gamma constant region CH1 exon (within the first 30 basepairs) as disclosed in Kabat et al. (supra).

One microgram of DNA was added to a 200 micromolar solution of each dATP, dCTP, dGTP and dTTP, with 100 pmoles of each primer and 5 units of Taq DNA polymerase (Promega Corp., Madison, Wis.). PCR cycles were as follows: denaturation at 98° C. for 3 minutes, annealing at 55° C. for 2 minutes and extension at 72° C. for 3 minutes, controlled in a DNA thermal cycler (Perkin Elmer Cetus).

Isolation, Cloning and Sequencing of the Amplified Products

Amplified DNA was size selected on a 1.0% low melting agarose gel, ligated into the EcoRV site of a phagemid vector (Bluescript, Stratagene Inc., La Jolla, Calif.), and transformed into $CaCl_2$ competent BSJ72 bacteria. Single stranded DNA for sequencing was isolated from each positive clone after superinfection with M13K07 (Biorad, Richmond, Calif.) as described (Sans, I. et al., supra). Sequencing was accomplished using dideoxy chain termination as described (Sanger, F. et al. *J. Mol. Biol.* 143:151, 1980) except using a modified T7 DNA polymerase (Sequenase U.S. Biochemicals, Cleveland Ohio) as described in Tabor, S., et al. (*Proc. Natl. Acad. Sci USA* 84:4767, 1987). Sequencing was performed in both orientations.

The sequences that were determined for human monoclonal antibodies 120-16 and 98-6, respectively are set forth in FIGS. 5 and 6.

In FIGS. 5 and 6, the top DNA strand is the coding sequence and the lower case letters under the sequences are the amino acid residues encoded by the mRNA. The designations "." and "+" between the two DNA strands are placed at intervals of five nucleotides for spacing. The single letter codes for the amino acid residues are as follows:

Alanine, a; Glycine, g; Valine, v; Isoleucine, i; Leucine, l; Histidine, h; Proline, p; Cystine, c; Threonine, t; Serine, s; Lysine, k; Arginine, r; Asparagine, n; Glutamic acid, e; Aspartic acid, d; Glutamine, q; Methionine, m; Phenylalanine, f; Tyrosine, y; Tryptophan, w.

Referring to FIGS. 5 and 6, it can be seen that the cDNA encoding the mRNA for the heavy chain of human monoclonal antibody 98-6 was 417 nucleotides in length and encoded 139 amino acids residues. The cDNA encoding the mRNA for the heavy chain of human monoclonal antibody 120-16 comprised 429 nucleotides that encoded 143 amino acid residues.

EXAMPLE 8

Further Epitope Mapping of Anti-gp41 Monoclonal Antibodies

Heterohybridoma production

Heterohybridomas, designated by the suffix "D", were derived by fusing the EBV transformed cells with the SHM-D33 mouse×human heteromyeloma cells (available as ATCC CRL 1668 from the American Type Culture Collection, Rockville, Md.). Briefly, the SHM-D33 cells were mixed with the lymphoblastoid cells at a ratio of 1:3, cenrifugated and treated with 1 ml of 50% polyethylene glycol (1300–1600 M.W., Sigma Chemicals, St. Louis, Mo.). After gradual dilution with Iscove's medium, the cells were gently centrifuged, suspended and plated in medium at $8 \times 10^4$ cells/well. After 24 hr., $10^4$ mouse peritoneal cells were added as feeder cells and the cultures were incubated in the presence of 0.5 mM hypoxanthine, 0.2 micromolar aminopterin, 16 micromolar thymidine and 1 micromolar ouabain. After 2–3 weeks, wells were screened for antibody production and those wells which were positive were expanded and sequentially, cloned at 100, 25 and 1 cell per well.

The specificity and subclass of the heterohybridomas was as follows:

| Line Designation | Specificity | Subclass |
|---|---|---|
| 181-D | gp41 | $IgG_2k$ |
| 240-D | gp41 | $IgG_1k$ |
| 246-D | gp41 | $IgG_1k$ |
| 167-D | gp41 | $IgG_1l$ |

Immunoglobulin assays

Antibody subclasses were determined by ELISA. Briefly, Immunolon 2 plates were coated with HIV viral lysate (4 micrograms/ml, ENI Diagnostic, Inc., Silver Springs, Md.) and incubated with culture suspernatants. The subtype of the mAb was detected by alkaline phosphatase labelled mouse mAb against the four subclasses of human IgG (Zymed Laboratories, Burlingame, Calif.).

The light chain type of each monoclonal antibody (mAb) was analysed by ELISA using microplates coated with rabbit anti-human kappa chain and rabbit anti-human lambda chain antibodies (Dakopatts, Kopenhagen, Denmark). The developing antibodies used were alkaline phosphatase-coupled goat anti-human kappa chain and goat anti-human lambda chain (Sigma Chemicals), respectively.

IgG quantitation was also performed by ELISA. The plates were coated with goat anti-human IgG (gamma-specific antibodies) and incubated with serially diluted culture supernatants. Bound IgG was detected with alkaline phosphatase-labelled goat anti-human IgG (gamma-specific) antibodies and incubated with serially diluted culture supernatants. Bound IgG was detected with alkaline phosphatase-labelled goat anti-human IgG (gamma-specific) antibodies. Affinity-purified human IgG (Organon-Teknika Cappel, Malvern, Pa.) was used as a standard. Plates were read and standard curves generated using an automated MR700 Microplate Reader (Dynatech, Chantilly, Va.).

Assays for inhibition of the binding of mAb to HIV viral lysate

Human mAb were biotinylated by a modification of the method of Liu and Green (*Clin. Chem.* 31:202, 1985) as described in Robinson et al. (*Proc. Nat. Acad. Sci. USA* 87 3185, 1970). Assays to measure the ability of unlabelled mAb or patients' sera to block the binding of biotinylated mAb to HIV viral lysate were performed as described in Robinson (Supra). For these assays, Immunolon 2 plates (Dynatech) were coated with 0.5 micrograms of HIV lysate in 100 microliters coating buffer and 100 microliters of culture supernatants, diluted 1–10–1:100 in phosphate-buffered saline, pH7.4 containing 10% normal goat serum, 0.5% Bovine serum albumin, or 100 microliters of human sera, diluted as above was added to each well. After incubation at room temperature overnight, the wells were washed and 100 microliters of biotinylated-mAb was added to each well. After a further incubation at 37° C. for 2 hr., ABTS substrate (Kirkeguard and Perry, Gaithersburg, Md.) was added and the color of the substance in the well read in an ELISA reader at 405 nm.

The following formula was used to determine the percent inhibition of binding:

$$\% \text{ Inhibition of binding} = \frac{A_{max} - A_x}{A_{max} - A_{min}} \times 100$$

where $A_{max}$ is the absorbance in the presence of diluent, $A_x$ is the absorbance of the sample being tested and $A_{min}$ is the absorbance in the presence of sufficient amounts of the mAb homologous to the biotinylated mAb used in the assay to give maximum inhibition (usually 0.3–5.0 micrograms/ml).

To titrate the 50% inhibition titer of human sera, the above-mentionned assay was performed using multiple dilutions of each patients' sera. The dilutions of each patient's serum ranged from 1:10 to 1:5×10⁶. Simultaneously, an inhibition curve was run to test the inhibitory capacity of the homologous mAb. The 50% inhibition titre of a given serum specimen was identified as the highest dilution of serum which gave at least 50% inhibition of the binding of the biotinylated mAb, as defined above.

Binding of mAb to synthetic and recombinant peptides by ELSIA

Synthetic peptides were prepared on an Applied Biosystem Inc. 430A peptide synthesizer (Foster City, Calif.) according to instructions supplied by the manufacturer. Peptides were deprotected and cleaved from the supporting resin with HF. Amino acid analysis was performed on all peptides to monitor content; all peptides employed had the expected amino acid content. Amino acid analysis on all synthetic peptides was performed by a commercial laboratory (Immunodynamics, Inc., La Jolla, Calif.).

Two peptides were purchased from commercial suppliers. The recombinant peptide, p121, an 82-mer spanning amino acids 560–642 encoded by the env gene was purchased from Centocor (Malverne, Pa.). This peptide was used at a concentration of 4 micrograms/well for coating ELISA plates. Peptide 6140 was purchased from American International Chemical Inc. (Natick, Mass.). This synthetic peptide spans amino acids 579–613 and contains a disulfide bridge between the two cysteines at positions 598 and 604. This peptide was used at a concentration of 0.25 ng/microgram/well for the coating of ELISA plates. Peptide 6140 was reduced and alkylated to test its reactivity after the cleavage of the disulfide bond. Thus, the peptide was suspended to a concentration of 2.5 micrograms/ml in coating buffer containing 100 mM of dithiothreotol. After incubation for 1 hr. at 37° C., an equal volume of 220 mM iodoacetamide in coating buffer was added. After another incubation for 1 hr at 37° C. the reduced and alkylated peptide was used to coat ELISA plates.

To identify the region of gp41 that binds human anti-gp41 mAb, 1 microgram synthetic peptides in 100 microliters of coating buffer was added to each well of Immunolon 2 microtitre plates. The plates were then incubated at 37° C. for 2 hr. The wells were then washed three times in PBS containing 0.05 % Tween 20. Undiluted culture supernatants containing mAb were added to each well. After incubation for 2 hr at 37° C., the wells were washed three times with washing buffer. Thereafter, goat anti-human IgG₁ (H+L, Bio-Rad, Richmond, Calif.) was added to each well at a dilution of 1:1000. The wells were then incubated for another hour at 37° C. Finally, ABTS was added to each well as substrate. The color in each well was detected at 405 nm after 30 min. Each assay was repeated at least three times with at least two different aliquots of mAb-containing supernatants.

Blocking experiments between anti-gp41 mAb reveal two groups of mAb

Figure 7A:
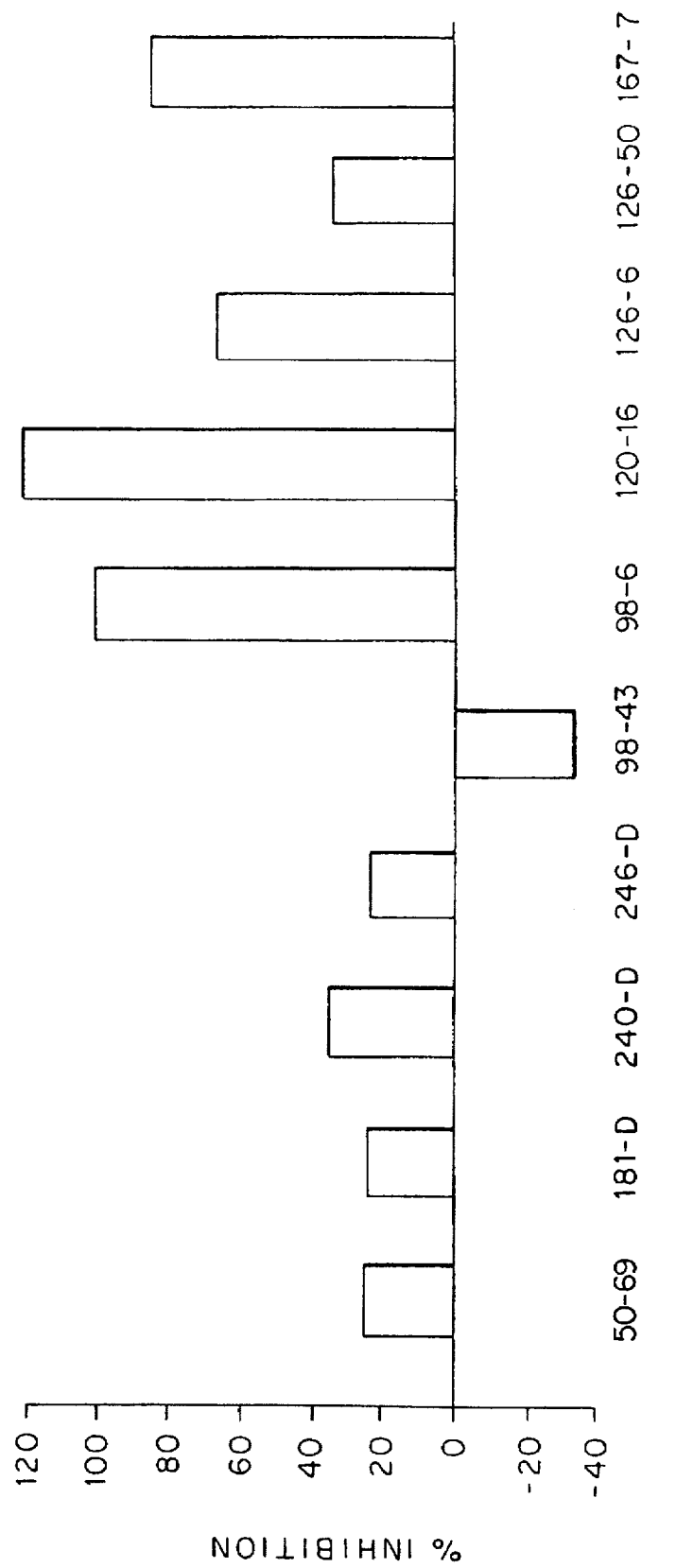
FIGS. 7A, 7B and 7C are a series of graph showing that the binding of biotinylated anti-gp41 antibodies is blocked by unlabeled gp41 monoclonal antibodies.
Figure 7B:
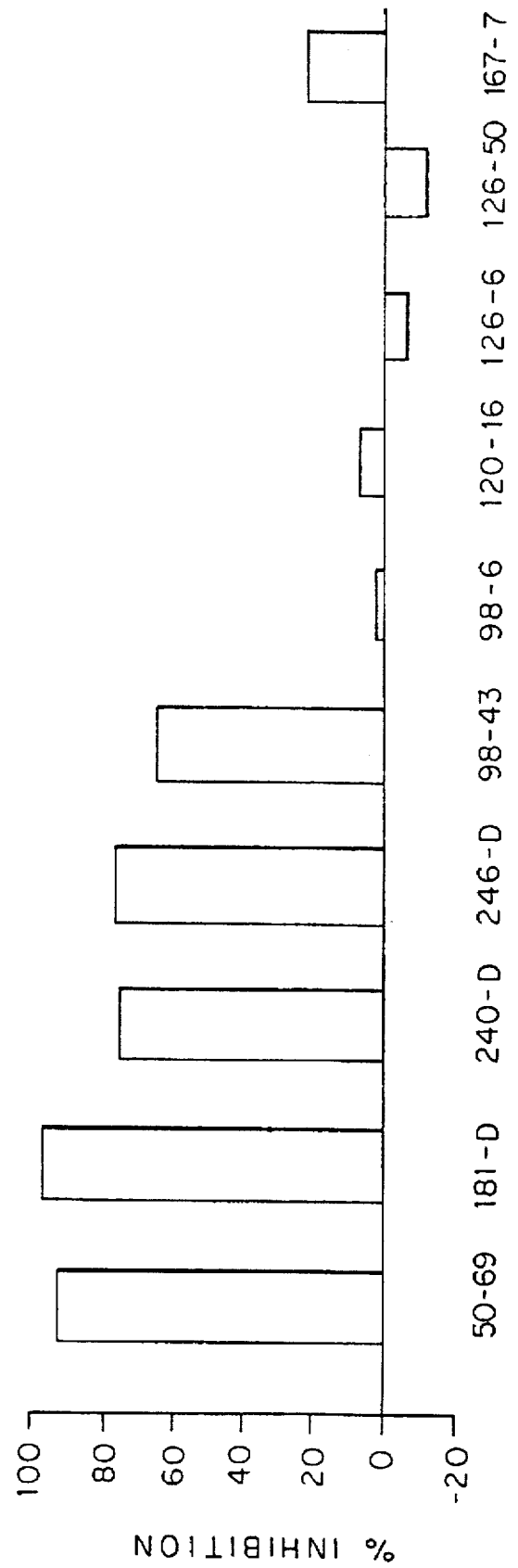
Figure 7C:
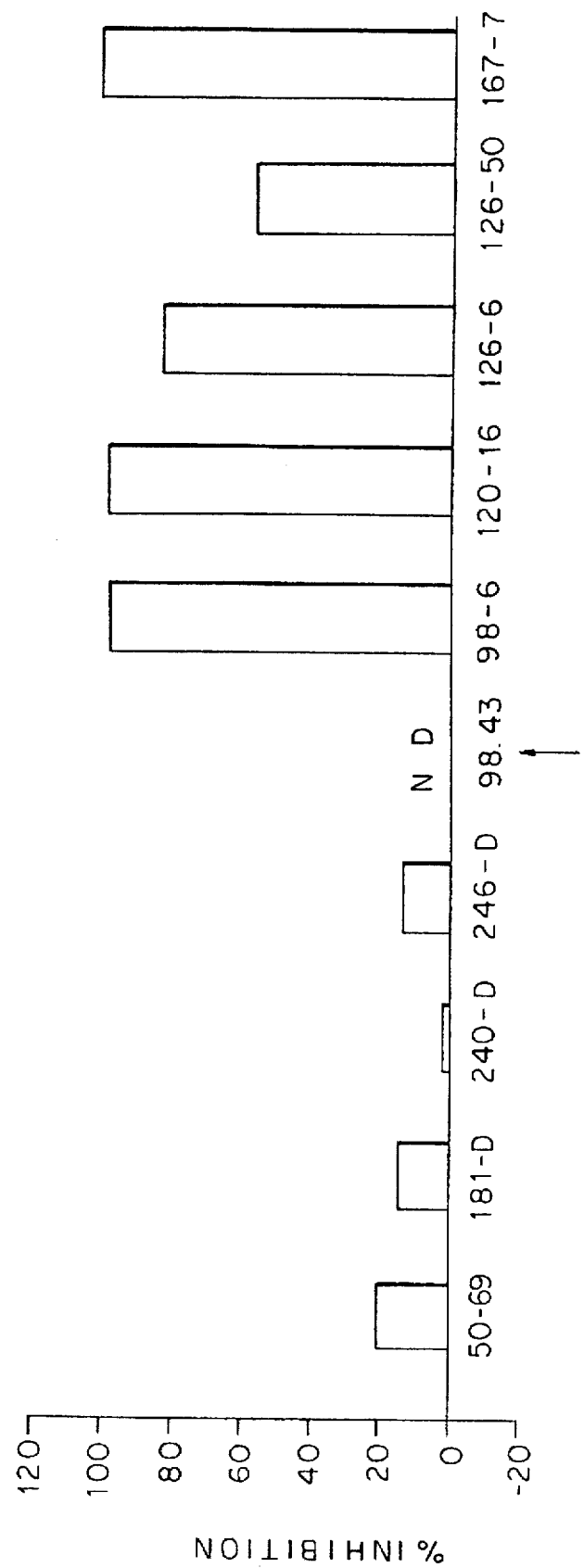
Figure 8:
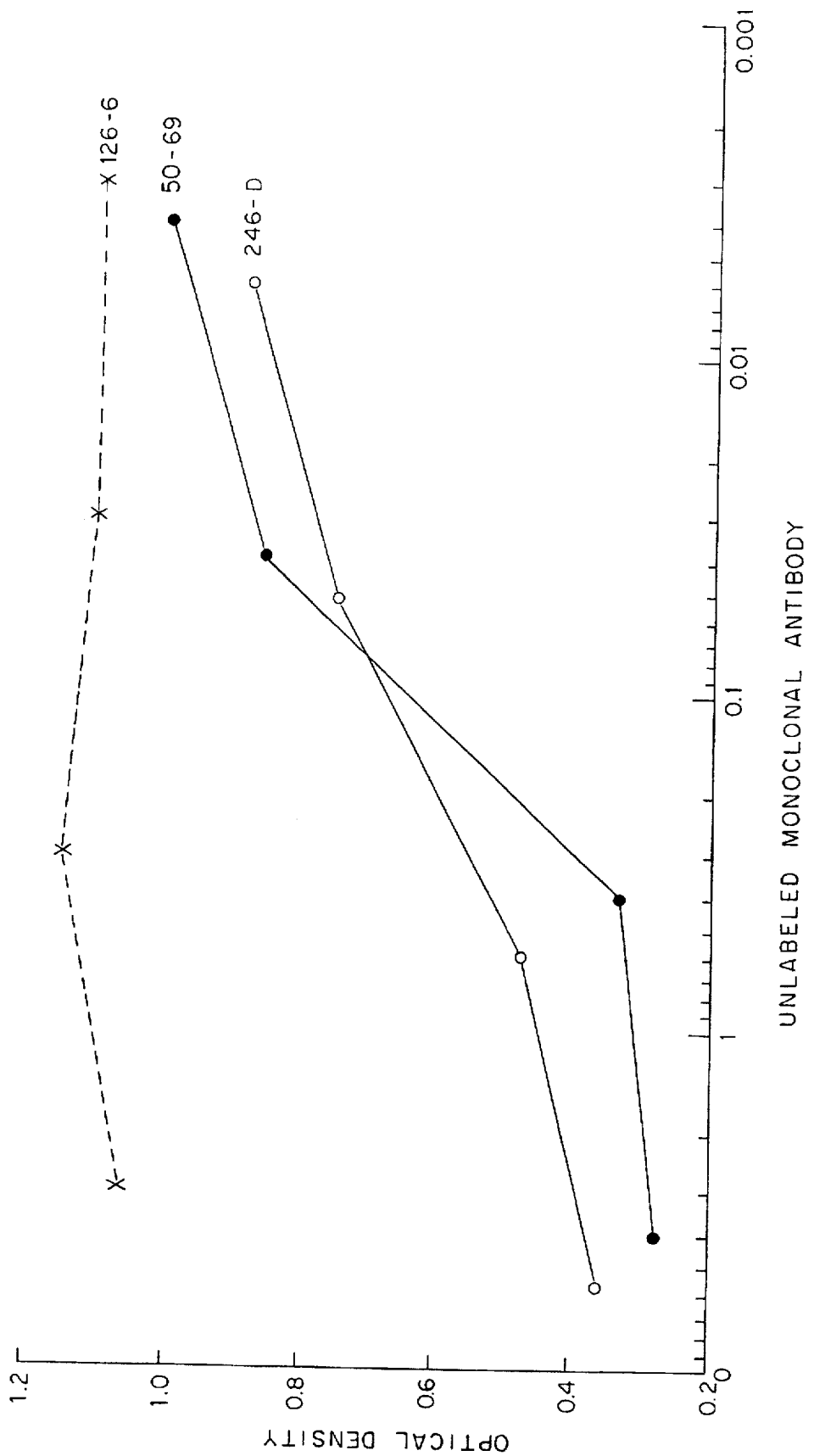
FIG. 8 is a graph showing the inhibition of binding of human monoclonal antibody 50-69 by monoclonal antibodies 246-D and 126-6.

Each mAb was biotinylated and tested for its ability to bind to HIV lysate in the presence of unlabelled mAb to gp41. The results of these experiments are shown in FIGS. 7(A–C). In these experiments, mAb 50-69(7B), 120-16(7C) and 98-6(7A) were tested against a panel of 10 unlabelled mAb to gp41. The results of these experiments are shown in FIGS. 7(A–C). In these experiments, mAb 50-69, 98-43, 181-D, 240-D and 246-D fall into a single group in which each member was able to inhibit the other members. Similarly, mAb 98-6, 120-16, 126-6, 126-50 and 167-7 constitute a second group related by specificity, a specificity that is distinct from the specificity of the former group. In FIG. 8, the ability of two mAb from group 1 and 2, (246-D and 126-6, respectively) to inhibit the binding of a group 1 mAb (50-69) is shown over a concentration range of four logs. Inhibition was still detectable within a single mAb group at a concentration as low as 0.006 micrograms/ml whereas a mAb from the heterologous group did not inhibit at a concentration of 3 micrograms/mi.

Peptide mapping of anti-gp41 mAb

In an initial attempt to locate the epitopes with which these two groups of mAb were reactive, each mAb was tested for its ability to bind to a commercially available recombinant peptide which encompasses 82 amino acids from the extracellular domain of gp41 (AA-560–641). The results are set forth in Table IV below.

TABLE IV

Reactivity of Human Anti-gp41 mAb Can Be Divided into Two Groups on the Basis of Reactivity with HIV Viral Lysate and a Recombinant Peptide (AA560-641)

| | O.D. 405 | |
|---|---|---|
| mAb | Peptide 560–641 | HIV lysate |
| 50–69* | >2.000 | 0.894 |
| 98–43* | >2.000 | 1.093 |
| 181-D* | >2.000 | 1.032 |
| 240-D* | >2.000 | 0.933 |
| 246-D* | >2.000 | 0.846 |
| 98–6+ | 0.135 | 0.911 |
| 120–16+ | 0.173 | 1.027 |
| 126–6+ | 0.218 | 1.079 |
| 126–50+ | 0.076 | 0.759 |
| 167-D+ | 0.176 | 0.917 |
| medium | 0.066 | 0.077 |

*categorized on the basis of data in FIG. 7 as members of a single cross-inhibitory group of mAb
+categorized on the basis of data in FIG. 7 as members of a second, cross-inhibitory group of mAb.

Table IV shows that those mAb which were categorized as belonging to the first group of cross-inhibitory mAb all bound to p121 whereas those mAb which belonged to the second group of cross-inhibitory mAb could not bind to p121.

To further localize the binding of the mAb, the panel of mAb was tested for reactivity against six synthetic peptides which span approximately 60% of the extracellular portion of the gp41. The results are set forth in Table V below:

TABLE V

Summary of Peptide Mapping of Human Monoclonal Antibodies to gp41

| | | Peptides from gp41* | | | | | |
|---|---|---|---|---|---|---|---|
| Monoclonal Antibody | Subclass | AA540–564 | AA579–604 | AA611–627 | AA644–663 | AA661–683 | AA703–721 |
| 50–69 | IgG$_2$k | – | – | – | – | – | – |
| 98–6 | IgG$_2$k | – | – | – | – | – | – |
| 98–43 | IgG$_2$k | – | + | – | – | – | – |
| 120–16 | IgG$_2$k | – | – | – | + | – | – |
| 126–50 | IgG$_2$k | – | – | – | – | – | – |
| 167–7 | IgG$_1$l | – | – | – | – | – | – |
| 181-D | IgG$_2$k | – | + | – | – | – | – |
| 240-D | IgG$_1$k | – | + | – | – | – | – |
| 246-D | IgG$_1$k | – | + | – | – | – | – |

*Los Alamos numbering system (Human Retroviruses and Aids Meyers, G. et al., eds, Theoretical Biology and Biophysics, 1989) which is the same as the Modrow System cited above.

Table V shows that four mAb (98-43, 181-D, 240-D and 246-D) react with peptide 41-12 which encompasses amino acids 576–604. All four of these mAb had been categorized as being cross-inhibitory on the basis of the blocking experiments shown in FIG. 7. Thus, four of the five mAb in group I were defined as being specific for linear sequences in the region of the extracellular disulfide loop of gp41, a region previously defined as a major immunodominant region. A single mAb (120-16) reacted with peptide 41-20 which encompasses amino acids 644–663. This latter mAb had previously been categorized as a member of the second group of mAb. Thus only one out of five mAb of the second group was to a linear sequence and the rest appeared to be specific for conformational or discontinuous epitopes.

Preliminary data had suggested that mAb 50-69, while not reacting to the linear peptide AA 579–604, did react with the Labsystems Kit (Finland), an ELISA kit which utilizes a peptide ranging from AA 599–613 to detect antibodies to gp41 (data not shown). In an attempt to identify the fine specificity of mAB 50-69, it was tested for reactivity against a peptide that spans AA 579–613 and contains a disulfide bridge between AA 598 and 604. Because this peptide is three to five times more sensitive in detecting HIV-1-positive serum reactivity than the same peptide which lacks the disulfide bridge, the peptide was reduced and alkylated to determine if mAb 50-69 represented an antibody that requires the presence of the disulfide bond. The results of a representative ELISA assay using these two related peptides are shown in Table VI.

TABLE VI

Reactivity of 50–69 Monoclonal Antibodies and Sera to peptide 579–613 with and without an intra-chain disulfide bond

| | Peptide AA 579–613 | |
|---|---|---|
| Sample | with disulfide bond | without disulfide bond |
| mAb 50–69 | 0.611* | 0.208 |
| mAb 246-D | 0.633 | 0.622 |
| mAb 98–6 | 0.224 | 0.225 |
| HIV-positive serum | 0.507 | 0.436 |
| HIV-negative serum | 0.211 | 0.189 |

*O.D. 405

Since mAb 50-69 reacted only with the cyclic form of the peptide and not with the reduced and alkylated form, and since mAb 50-69 did not react with peptide 579–604 (Table IV) which lacks the disulfide bond, the specificity of mAb 50-69 was shown to map to an area of gp41 which encompasses the two cysteines at AA 598 and 604 and requires that they be disulfide linked.

The mAb reacting with AA 579–604 (41-12) were studied further to define their fine specificity. Thus, each mAb reactive with this linear peptide was tested against a set of 21 hexapeptides which span this region. Each hexapeptide overlapped its neighbor by five amino acids. The hexapeptides, synthesized in situ on pins of the Epitope Mapping Kit, were reacted with supernatants of the four relevant cell lines which contained 5–10 micrograms mAb/ml. The results are set forth in Table VII below.

TABLE VII

| Pin # | Hexapeptide | 181-D | 246-D | 240-D |
|---|---|---|---|---|
| 3 | RILAVE | − | − | − |
| 4 | ILAVER | − | − | − |
| 5 | LAVERY | − | − | − |
| 6 | AVERYL | − | − | − |
| 7 | VERYLK | − | − | − |
| 8 | ERYLKD | − | − | − |
| 9 | RYLKDQ | − | − | − |
| 10 | YLKDQQ | − | − | − |
| 11 | LKDQQL | − | − | − |
| 12 | KDQQLL | − | − | − |
| 13 | DQQLLG | − | − | − |
| 14 | QQLLGI | − | + | − |
| 15 | QLLGIW | + | + | − |
| 16 | LLGIWG | + | + | + |
| 17 | LGIWGC | − | − | + |
| 18 | GIWGCS | − | − | + |
| 19 | IWGCSG | − | − | + |
| 20 | WGCSGK | − | − | − |
| 21 | GCSGKL | − | − | − |
| 22 | CSGKLI | − | − | − |
| 23 | SGKLIC | − | − | − |

As can be seen from the data set forth in Table VII, above mAB 181-D reacted with an epitope comprising 7 amino acids (QLLGIWG), mAB 240-D reacted with nonapeptide (LLGIWGCSG) and mAB 246-D reacted with an octapeptide (QQLLGIWG).

Titration of Serum Antibodies from HIV-Infected Patients to Epitope Clusters I and II of gp41

Several studies have noted the nearly universal appearance of antibody to the region of gp41 surrounding the cysteines at AA 598 and 604 (Goudsmit, J., *AIDS* 2 (Suppl. 1) 541, 1988; Klasse, P. J. et al., *Proc. Nat. Acad. Sci. USA* 85: 5225, 1988; Narvanen, A. et al., *AIDS* 2: 119, 1988; Gnann, J. W. et al., *J. Inf. Dis.* 156: 261, 1987), here designated as Cluster I. A much lower percentage of patients' sera react with the region that maps from approximately 644 to 663, i.e., Cluster II (Klasse et al., supra). The relative amounts of antibody to epitope Cluster I and II, in patients' sera were studied using inhibition assays. In these assays sera from seven HIV infected patients were tested for their ability to inhibit by 50% the binding to HIV lysates of biotinylated mAb specific for Cluster I (50-69) or cluster II (120-16). The sera tested were derived from patients at diverse stages of disease progression as previously defined (Zolla-Pazner, S. et al., *Proc. Nat. Acad. Sci USA* 84: 5404, 1987). One hundred percent inhibition of binding of the homologous labelled mAb was achieved with ≧300 ng/ml of mAb 50-69 and with ≧1375 ng/ml of mAb 120-16. Sera from seronegative volunteers gave no significant inhibition at a dilution of 1:10. The 50% inhibitory titres of the patients' sera are set forth in Table VIII below.

TABLE VIII

Titration of Patients' Sera for Antibodies to Epitope cluster I (AA 579–604) and Cluster II (AA 644–663)

| | Serum titres for 50% Inhibition of | |
|---|---|---|
| Patient No. | Biotinylated 50–69 | Biotinylated 120–16 |
| 1 (6) | 1:100,000 | 1:1,000 |
| 2 (7) | 1:100,000 | 1:5,000 |
| 3 (8) | 1:500,000 | 1:5,000 |
| 4 (11) | 1:500,000 | 1:10,000 |
| 5 (15) | 1:1,000,000 | 1:10,000 |
| 6 (47) | 1:100,000 | 1:1,000 |
| 7 (48) | 1:100,000 | 1:1,000 |
| Geometric Mean Titre | 1:220,220 | 1:2,200 |

The geometric mean titre for 50% inhibition of binding of 50-69 (mAb to Cluster I) was 1:220,000. The geometric mean titre for 50% inhibition of binding of 120-16 (mAb to Cluster II) was 1:2200. Thus, the epitopes of Cluster I appear to be approximately one hundred-fold more immunogenic than those represented in Cluster II.

What is claimed is:

1. A human monoclonal antibody which specifically binds to an epitope of Human Immunodeficiency Virus-1 protein gp41 and which competes with the binding of 120-16 to gp41.

2. A fragment of a human monoclonal antibody which specifically binds to an epitope of Human Immunodeficiency Virus-1 protein gp41 and which competes with the binding of 120-16 to gp41.

3. A fragment in accordance with claim 2, wherein said fragment is the Fab or F(ab')$_2$ fragment of said antibody.

4. A human lymphoblastoid cell line producing a human monoclonal antibody in accordance with claim 1.

5. The human lymphoblastoid cell line of claim 4 derived from a human infected with human immunodeficiency virus.

6. A human monoclonal antibody in accordance with claim 1 and having the ability to mediate antibody-dependent cellular cytotoxicity when measured in an assay using peripheral blood mononuclear cells as effectors and CEM.NKR cell line, infected with HTLV-IIIB, MN and RF, as targets.

7. The monoclonal antibody of claim 6 wherein said monoclonal antibody is of the IgG isotype.

8. A human lymphoblastoid cell line producing a human monoclonal antibody according to claim 6.

9. A human lymphoblastoid cell line according to claim 8, which is derived from a human infected with human immunodeficiency virus-1.

10. A human monoclonal antibody which specifically binds to an immunodominant region of HIV-1 protein gp41 in the region of 644–663.

11. A fragment of a human monoclonal antibody which specifically binds to an immunodominant region of HIV-1 protein gp41 in the region of 644–663.

12. A fragment in accordance with claim 11, wherein said fragment is the Fab or F(ab')$_2$ fragment of said antibody.

13. A human lymphoblastoid cell line producing a human monoclonal antibody in accordance with claim 10.

14. A human monoclonal antibody which specifically binds to an epitope within the region 644–663 of Human Immunodeficiency Virus-1 protein gp41, said monoclonal antibody having the ability to mediate antibody-dependent cellular cytotoxicity when measured in an assay using peripheral blood mononuclear cells as effectors and CEM.NKR cell line, infected with HTLV-IIIB, MN and RF, as targets.

15. The monoclonal antibody of claim 14, wherein said monoclonal antibody is of the IgG type.

16. A human lymphoblastoid cell line producing a human monoclonal antibody according to claim 14.

17. A human lymphoblastoid cell line according to claim 16, which is derived from a human infected with Human Immunodeficiency Virus-1.

18. A human monoclonal antibody which specifically binds to an epitope within the region 644–663 of Human Immunodeficiency Virus-1 protein gp41.

19. A fragment of a human monoclonal antibody which specifically binds to an epitope within the region 644–663 of Human immunodeficiency Virus-1 protein gp41.

20. An isolated molecule comprising a fragment of a human antibody, which fragment specifically binds to an epitope with human immunodeficiency virus-1 protein gp41 which competes with the binding of 120-16 to gp41.

21. An isolated molecule comprising a fragment of a human antibody, which portion specifically binds to an immunodominant region of HIV-1 protein gp41 in the region of 644–663.

* * * * *